(12) United States Patent
Holliday et al.

(10) Patent No.: US 11,878,180 B2
(45) Date of Patent: Jan. 23, 2024

(54) AUTOMATED EXTERNAL DEFIBRILLATOR SYSTEMS WITH POWER CHARGING FEATURES

(71) Applicants: Annika Ulrike Holliday, Portland, OR (US); Lucas George Holliday, Portland, OR (US)

(72) Inventors: Annika Ulrike Holliday, Portland, OR (US); Lucas George Holliday, Portland, OR (US)

( * ) Notice: Subject to any disclaimer, the term of this patent is extended or adjusted under 35 U.S.C. 154(b) by 0 days.

(21) Appl. No.: 17/034,731

(22) Filed: Sep. 28, 2020

(65) Prior Publication Data
US 2021/0008380 A1    Jan. 14, 2021

Related U.S. Application Data

(60) Provisional application No. 62/907,866, filed on Sep. 30, 2019.

(51) Int. Cl.
    *A61N 1/39*    (2006.01)

(52) U.S. Cl.
    CPC .......... *A61N 1/3904* (2017.08); *A61N 1/3975* (2013.01)

(58) Field of Classification Search
    CPC ...................... A61N 1/3904; A61N 1/3975
    See application file for complete search history.

(56) References Cited

U.S. PATENT DOCUMENTS

| | | | |
|---|---|---|---|
| 2002/0169482 A1* | 11/2002 | SerVaas | A61N 1/39 607/5 |
| 2003/0080712 A1* | 5/2003 | Tamura | A61N 1/3975 320/103 |
| 2004/0267322 A1* | 12/2004 | Kavounas | A61N 1/3975 607/5 |
| 2008/0046038 A1* | 2/2008 | Hill | A61N 1/37276 607/60 |
| 2010/0063559 A1* | 3/2010 | Mcintyre | A61N 1/3904 607/5 |
| 2011/0046688 A1* | 2/2011 | Schwibner | G06F 21/31 607/5 |
| 2016/0206894 A1* | 7/2016 | Kuo | A61N 1/3968 |
| 2017/0367927 A1* | 12/2017 | Cervantes | G16H 40/63 |
| 2019/0232068 A1* | 8/2019 | Lancaster | A61N 1/3904 |
| 2020/0054885 A1* | 2/2020 | Aprile | G07C 9/38 |
| 2020/0360707 A1* | 11/2020 | Christiansen | H02J 7/0045 |
| 2020/0398066 A1* | 12/2020 | Teber | A61N 1/3968 |

* cited by examiner

*Primary Examiner* — Eric D. Bertram
(74) *Attorney, Agent, or Firm* — Mohr Intellectual Property Law Solutions, PC (57) ABSTRACT

Automated external defibrillator systems including an automated external defibrillator and a charging device. The automated external defibrillator includes a countercheck device and a single treatment battery. The countershock device is configured to deliver automated external defibrillation treatment to a person. The single treatment battery is electrically coupled to the countershock device and has a power storage capacity selected to store power sufficient for the countershock device to operate for a single treatment scenario. The charging device is configured to couple to the single treatment battery and to transfer power to the single treatment battery for the single treatment battery to store. In some examples, the automated external defibrillator system includes a housing.

19 Claims, 5 Drawing Sheets

AUTOMATED EXTERNAL DEFIBRILLATOR SYSTEMS WITH POWER CHARGING FEATURES

CROSS REFERENCE TO RELATED APPLICATIONS

This application claims priority to copending U.S. Application, Ser. No. 62/907,866, filed on Sep. 30, 2019, which is hereby incorporated by reference for all purposes.

BACKGROUND

The present disclosure relates generally to automated external defibrillator systems. In particular, automated external defibrillator systems with power charging features are described.

Atrial fibrillation, or AFib, is a common form of heart attack that can cause serious medical complications or death. Society's increasing awareness of atrial fibrillation is evident by atrial fibrillation detection features incorporated into popular consumer electronic devices, such the Apple Watch™ device.

An important method to improve the chances of someone surviving an atrial fibrillation event involves delivering electric current between 100 and 400 Joules, known as a countershock, to the heart to correct the rhythm. Defibrillation treatments can be provided by trained medical personnel or by laypersons with the aid of automated external defibrillators, known as AEDs.

The likelihood of surviving an atrial fibrillation event, however, decreases approximately 10% per minute, so one or more countershocks from an AED within 10 minutes or less of the onset of the atrial fibrillation event is necessary to be effective. A countercheck is recommended every 2 minutes with CPR in between to keep blood flowing. Assuming survival past 10 minutes is unlikely, an AED device holding 5 to 10 shocks is perhaps the most that would be useful or necessary before either resuming a normal heart rhythm or death.

Typical AEDs are designed to hang on a wall behind glass with a battery providing five years of battery life and a service life of 200 uses even though most are never used even once. Batteries of this size and capacity are cumbersome and expensive, which limits the availability of AEDs despite there being many people and locations which would benefit from having AEDs present.

Further, batteries with a limited effective battery life must be replaced prior to the battery life expiring. The need to replace batteries requires robust maintenance procedures and introduces significant expense. A significant risk with limited battery life AEDs is that a given AED will not be replaced or have its battery replaced despite being beyond the battery's power storage life.

Another limitation of existing AEDs is that people do not know if they are available at a given location or where to find them. In an emergency event where someone is experiencing an atrial fibrillation event, people nearby seeking to help need to be able to quickly and reliably know where to locate an AED. Even if there is an AED nearby somewhere on the premises, there is a distinct risk that people seeking to help will not know the AED is nearby or where to find it.

Thus, there exists a need for AED systems that improve upon and advance die design of known AEDs. Examples of new and useful AED systems relevant to the needs existing in the field are discussed below.

SUMMARY

The present disclosure is directed to the automated external defibrillator systems including an automated external defibrillator and a charging device. The automated external defibrillator includes a countershock device and a single treatment battery. The countershock device is configured to deliver automated external defibrillation treatment to a person. The single treatment battery is electrically coupled to the countershock device and has a power storage capacity selected to store power sufficient for the countershock device to operate for a single treatment scenario. The charging device is configured to couple to the single treatment battery and to transfer power to the single treatment battery for the single treatment battery to store. In some examples, the automated external defibrillator system includes a housing.

DETAILED DESCRIPTION

The disclosed automated external defibrillator systems will become better understood through review of the following detailed description in conjunction with the figures. The detailed description and figures provide merely examples of the various inventions described herein. Those skilled in the art will understand that the disclosed examples may be varied, modified, and altered without departing from the scope of the inventions described herein. Many variations are contemplated for different applications and design considerations; however, for the sake of brevity, each and every contemplated variation is not individually described in the following detailed description.

Throughout the following detailed description, examples of various automated external defibrillator systems are provided. Related features in the examples may be identical, similar, or dissimilar in different examples. For the sake of brevity, related features will not be redundantly explained in each example. Instead, the use of related feature names will cue the reader that the feature with a related feature name may be similar to the related feature in an example explained previously. Features specific to a given example will be described in that particular example. The reader should understand that a given feature need not be the same or similar to the specific portrayal of a related feature in any given figure or example.

Definitions

The following definitions apply herein, unless otherwise indicated.

"Substantially" means to be more-or-less conforming to the particular dimension, range, shape, concept, or other aspect modified by the term, such that a feature or component need nor conform exactly. For example, a "substantially cylindrical" object means that the object resembles a cylinder, but may have one or more deviations from a true cylinder.

"Comprising," "including," and "having" (and conjugations thereof) are used interchangeably to mean including hut not necessarily limited to, and are open-ended terms not intended to exclude additional elements or method steps not expressly recited.

Terms such as "first", "second", and "third" are used to distinguish or identify various members of a group, or the like, and are not intended to denote a serial, chronological, or numerical limitation.

"Coupled" means connected, other permanently or releasably, whether directly or indirectly through intervening components.

Automated External Defibrillator System with Power Charging Features

With reference to the figures, automated external defibrillator systems with power charging features will now be described. The automated external defibrillator systems discussed herein function to provide automated external defibrillation treatment and to electrically couple to external power sources to maintain adequate power reserves.

The reader will appreciate from the figures and description below that the presently disclosed automated external defibrillator systems address many of the shortcomings of conventional automated external defibrillators. For example, the AED systems disclosed herein include charging capabilities enabling them to maintain the charge of their batteries over extended periods of time unlike conventional AEDs, which rely on batteries with limited lifespans. Whereas currently known AEDs must be tracked, maintained, and/or replaced to contend with onboard batteries limited useful lives, the presently described AED systems maintain adequate power reserves well beyond the useful life of conventional AEDs by recharging their batteries as needed.

The currently described AED systems avoid the expense and cumbersome size of batteries utilized in conventional AEDs that are selected to last for approximately five years. Instead of relying on a large, expensive battery to provide power reserves for years and years, the presently described AED systems utilize economical and compact batteries that provide enough power for automated external defibrillation treatment without excess capacity for years of additional power storage. The relatively inexpensive and compact design of the batteries utilized in the AED systems described herein allow the AED systems to be more affordable and readily available. The improved availability improves the chances that an AED system described in this application would be available in the event of an atrial fibrillation event.

Another improvement over conventional AEDs is that the currently described AED systems enable the AED systems to be widely deployed and stored in places reliably close at hand. For example, the AED systems described here may be stored in vehicles, such as in the glove box of a vehicle. Almost every vehicle could have one of the present AED systems stored in it to have on hand, which would allow people to consistently know where to find one in the event of an emergency. The ready and reliable availability of the AED systems described herein contrast with conventional AEDs that are stored in inconsistent, fixed, and often unknown locations of buildings and public spaces.

Contextual Details

Ancillary features relevant to the automated external defibrillator systems described herein will first be described to provide context and to aid the discussion of the automated external defibrillator systems.

Vehicle

Figure 1:
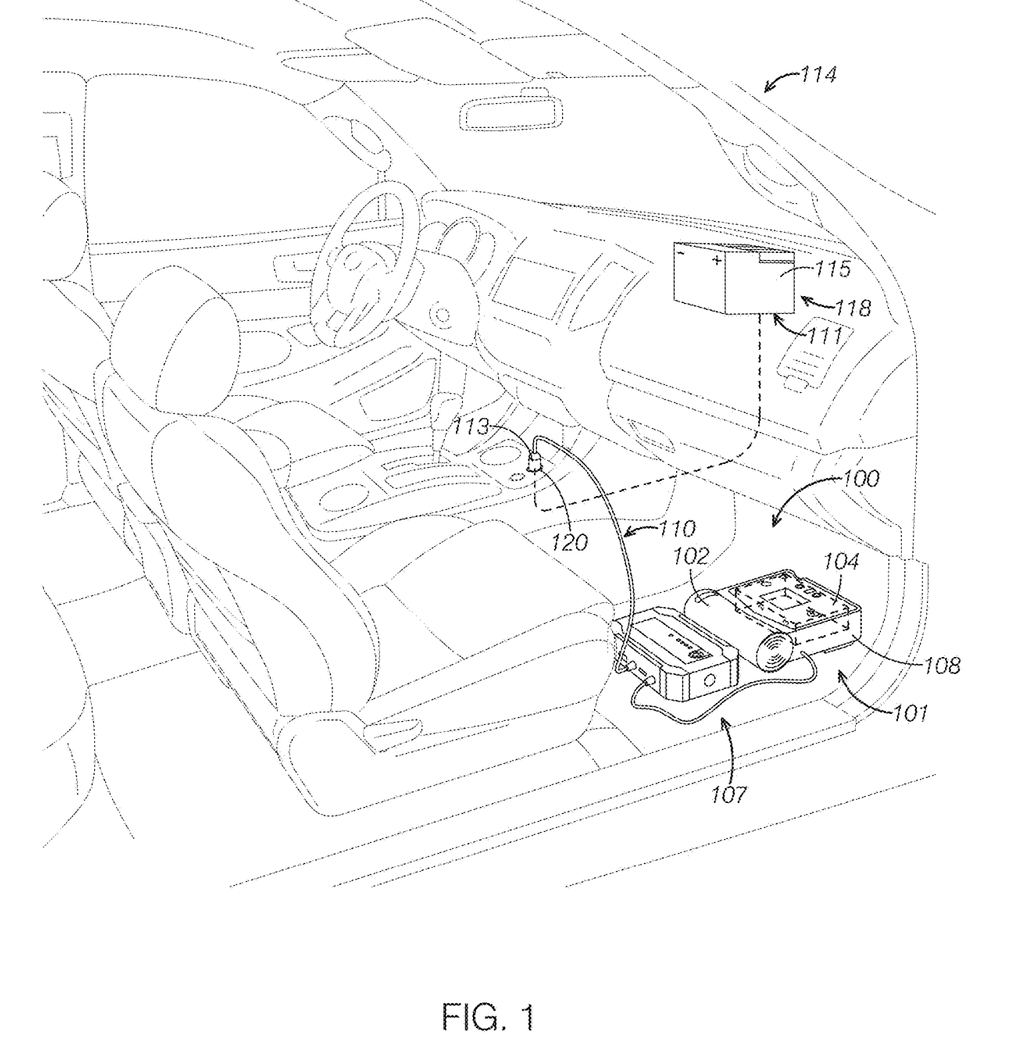
FIG. 1 is a conceptual view of an automated external defibrillator (AED) system mounted in the footwell of a vehicle, the AED system including an AED device coupled to a charging device, which is coupled to an auxiliary power socket of the vehicle via an auxiliary power outlet plug.

The automated external defibrillator systems described herein may be stored in vehicles and connect to vehicle power sources, such as shown in FIG. 1 where automated external defibrillator system 100 is stored in a vehicle 114. The reader can see in FIG. 1 that vehicle 114 includes a vehicle battery 115.

The vehicle may be any currently known or later developed type of vehicle. The reader will appreciate that a variety of vehicle types exist and could be used in place of the vehicle shown in the figures. In addition to the types of vehicles existing currently, it is contemplated that the automated external defibrillator systems described herein could be used with new types of vehicles developed in the future.

External Power Source

The automated external defibrillator systems described herein are configured to electrically couple to external power sources. The external power source may be any currently known or later developed type of external power source. Suitable types of external power sources include vehicle power sources; batteries, such as electronic device batteries; capacitors; fuel cells; or utility power accessible via a wall outlet.

The reader will appreciate that a variety of external power source types exist and could be used in place of the external power sources shown in the figures. In addition to the types of external power sources existing currently, it is contemplated that the automated external defibrillator systems described herein could utilize new types of external power sources developed in the future.

Vehicle Power Source

One example of an external power source utilized by automated external defibrillator systems described below is a vehicle power source 118. Vehicle power source 118 includes vehicle battery 115. Vehicle 118 includes a vehicle auxiliary power socket 120 electrically coupled to vehicle battery 115. Common locations for vehicle power connection sockets or ports include center consoles, glove boxes, and trunks.

The vehicle power source may be any currently known or later developed type of vehicle power source, such as a vehicle battery or electricity generator. The reader will appreciate that a variety of vehicle power source types exist and could be used in place of the vehicle power source shown in the figures. In addition to the types of vehicle power sources existing currently, it is contemplated that the automated external defibrillator systems described herein could incorporate new types of vehicle power sources developed in the future.

Automated External Defibrillator System

Figure 2:
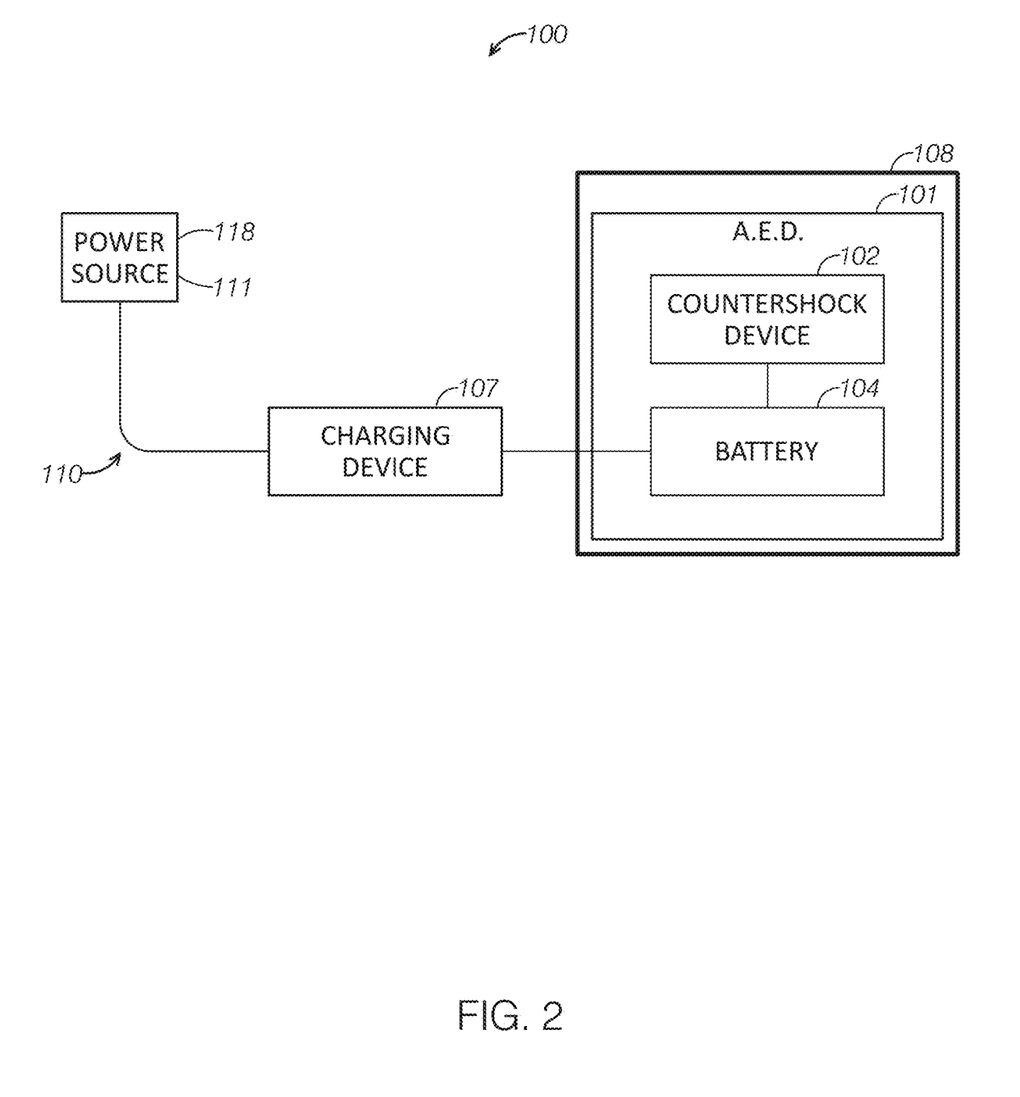
FIG. 2 is a schematic view of the AED system shown in FIG. 1 depicting a housing containing the AED device, the AED device including a countershock device and a single treatment battery, and the charging device disposed outside the housing and selectively coupled to the single treatment battery via a cable.

With reference to FIGS. 1 and 2, an automated external defibrillator system 100 will now be described as a first example of an automated external defibrillator system. Automated external defibrillator system 100 functions to provide automated external defibrillation treatment and to electrically couple to vehicle power source 118 to maintain adequate power reserves.

As shown in FIGS. 1 and 2, automated external defibrillator system 100 includes an automated external defibrillator 101, a charging device 107, and a housing 108. In other examples, the automated external defibrillator system includes fewer components than depicted in the figures. In certain examples, the automated external defibrillator system includes additional or alternative components than depicted in the figures.

In the example shown in FIG. 1, automated external defibrillator system 100 is stored in a footwell of vehicle 114 and is electrically coupled to vehicle battery 115 of vehicle 114. Electrically coupling to vehicle battery 115 of vehicle 114 enables charging device 107 to recharge single treatment battery 104 utilized by automated external defibrillator system 100 regularly as needed. Of course, the AED system could connect to power sources other than a battery of a vehicle, such as utility power in a building, a solar power source, a battery in another device, such as a computer or cell phone, or a specially configured power source.

By regularly charging its battery from power supplied by the vehicle, the battery life of automated external defibrillator system 100 is extended beyond the life it would otherwise have without access to a power source to replenish its reserves. Further, the size of the battery, and in particular, its energy storage capacity, can be significantly smaller than batteries must be in conventional AEDs. The smaller size and storage capacity of the battery in automated external defibrillator system 100 shown in FIG. 1 reduces the cost of the battery significantly.

The shape of the automated external defibrillator system may be adapted to be different than the specific examples shown in the figures to suit a given application. For example, the automated external defibrillator system may include a face having the shape of a regular or irregular polygon, such as a circle, oval, triangle, square, rectangle pentagon, and the like. Additionally or alternatively, the automated external defibrillator system may include a face having an irregular shape. In three dimensions, the shape of the automated external defibrillator system may be a sphere, a pyramid, a cone, a cube, and variations thereof, such as a hemisphere or a frustoconical shape.

The size of the automated external defibrillator system may be varied as needed for a given application. In some examples, the automated external defibrillator system is larger relative to the other components dun depicted in the figures. In other examples, the automated external defibrillator system is smaller relative to the other components than depicted in the figures, further, the render should understand that the automated external defibrillator system and the other components may all be larger or smaller than described herein while maintaining their relative proportions.

Automated External Defibrillator

Figure 5:
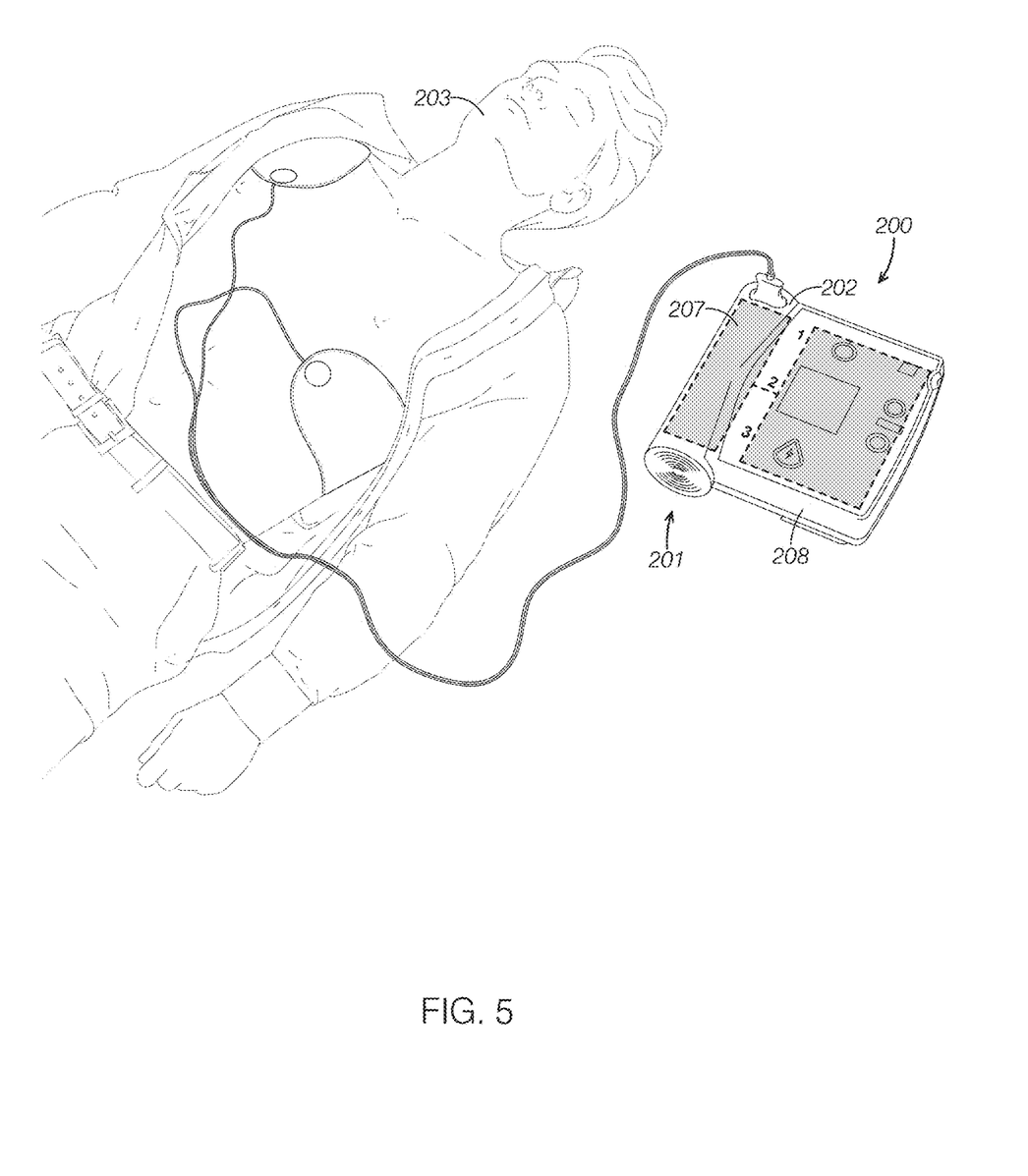
FIG. 5 is a perspective view of the AED system shown in FIG. 3 being used to provide automated external defibrillation treatment to a person lying on the ground.

Automated external defibrillator 101 functions to provide automated external defibrillation treatments. A person 203 receiving automated external defibrillation treatment from a similar automated external defibrillator, automated external defibrillator 201, is depicted in FIG. 5.

The reader can see in FIG. 2 that automated external defibrillator 101 includes a countershock device 102 and a single treatment battery 104. As depicted in FIG. 1, automated external defibrillator 101 is configured to be stored in a vehicle 114.

Automated external defibrillator 101 shown in FIGS. 1 and 2 may be described as a single use device in the sense that if is intended to store just enough power to provide countershocks during a single atrial fibrillation event. From a medical and practical standpoint, the power reserves needed may be only 10 minutes worth of power given that the medical consequences result beyond 10 minutes in an atrial fibrillation event. In actuality, the AED may store power sufficient to provide countershocks for multiple atrial fibrillation events and/or for longer than 10 minutes, such as 20 to 60 minutes, or however much time is deemed necessary from a safety factor standpoint, automated external defibrillator system 100 shown in FIG. 1 is intended to utilize a smaller onboard power source than conventional AEDs and to regularly replenish its power supply by drawing power from an external power source.

The size of the automated external defibrillator may be varied as needed for a given application. In some examples, the automated external defibrillator is latter relative to the other components than depicted in the figures. In other examples, the automated external defibrillator is smaller relative to the other components than depicted in the figures. Further, the reader should understand that the automated external defibrillator and the other components may all be larger or smaller than described herein while maintaining their relative proportions.

The shape of the automated external defibrillator may be adapted to be different than the specific examples shown in the figures to suit a given application. For example, the automated external defibrillator may include a face having the shape of a regular or irregular polygon, such as a circle, oval, mangle, square, rectangle pentagon, and the like. Additionally or alternatively, the automated external defibrillator may include a face having an irregular shape. In three dimensions, the shape of the automated external defibrillator may be a sphere, a pyramid, a cone, a cube, and variations thereof, such as a hemisphere or a frustoconical shape.

The automated external defibrillator may be any currently known or later developed type of automated external defibrillator. The reader will appreciate that a variety of automated external defibrillator types exist and could be used in place of the automated external defibrillator shown in the figures. In addition to the types of automated external defibrillators existing currently, it is contemplated that the automated external defibrillator systems described herein could incorporate new types of automated external defibrillators developed in the future.

Countershock Device

Figure 3:
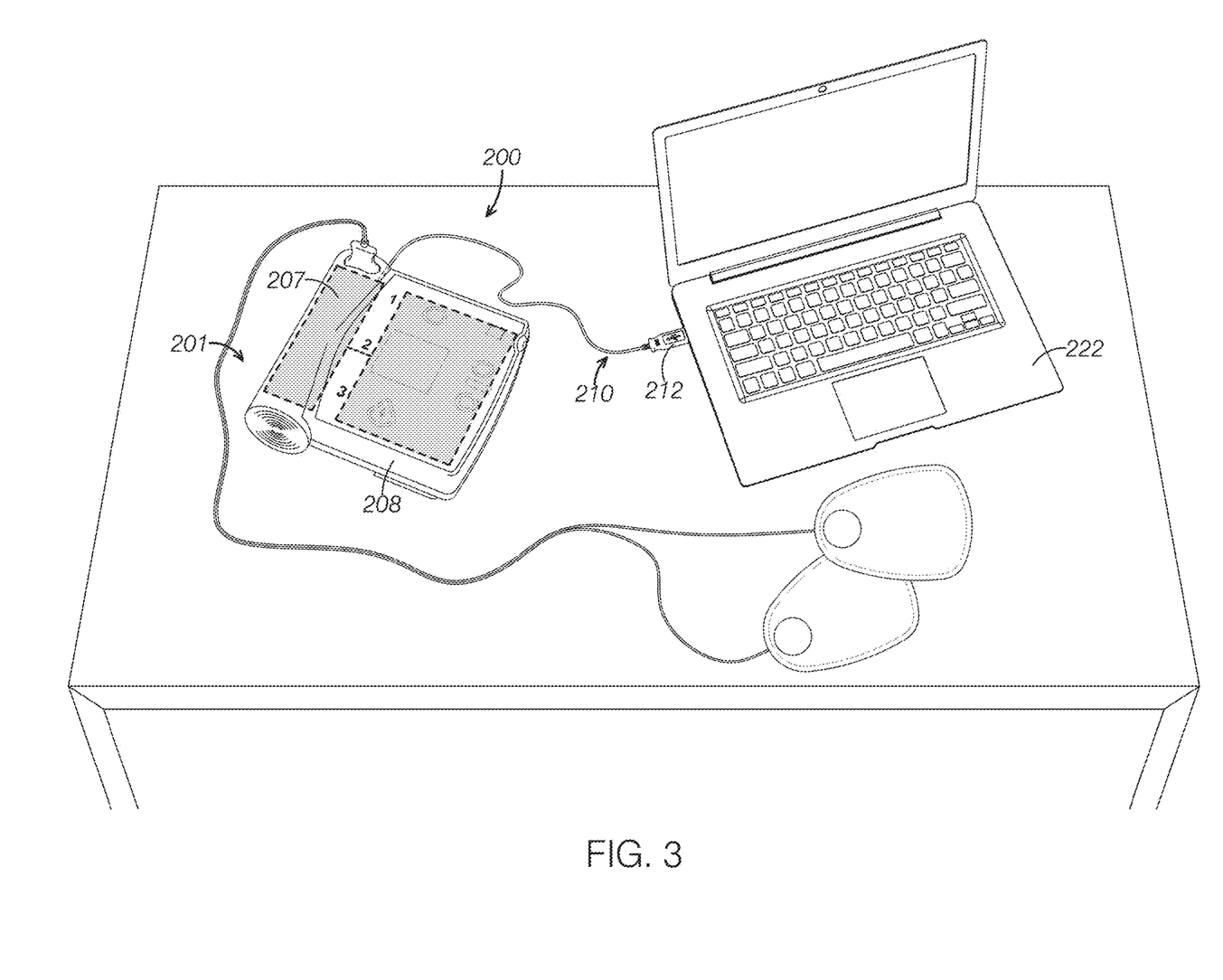
FIG. 3 is a conceptual view of an AED system resting on a desk, the AED system including an AED device with an integrated charging device, the charging device including a USB cable connected to a USB port of a computer.

Countershock device 102 depicted in FIGS. 1 and 2 is configured to deliver automated external defibrillation treatment to a person. A person 203 receiving automated external defibrillation treatment from a similar counters hock device included in automated external defibrillator 201 is depicted in FIG. 3.

The countershock device may be any currently known or later developed type of countershock device. The reader will appreciate that a variety of countershock device types exist and could be used in place of the countershock device shown in the figures. In addition to the types of countershock devices existing currently, it is contemplated that the automated external defibrillator systems described herein could incorporate new types of countershock devices developed in the future.

The size of the countershock device may be varied as needed for a given application. In some examples, the countershock device is larger relative to the other components than depicted in the figures. In other examples, the countershock device is smaller relative to the other components than depicted in the figures. Further, the reader should understand that the countershock device and the other components may all be larger or smaller than described herein while maintaining their relative proportions.

Single Treatment Battery

The role of single treatment battery 104 is to store energy for countershock device 102 to use to deliver automated external defibrillation treatment to a person. The reader should understand that in some examples, a power storage component other than a battery may be used, such as a capacitor or fuel cell.

As shown in FIG. 2, single treatment battery 104 is electrically coupled to countershock device 102 and to charging device 107. Single treatment battery 104 being electrically coupled to countershock device 102 enables countershock device 102 to draw energy from single treatment battery 104 as needed.

Single treatment battery 104 has a power storage capacity selected to store power sufficient for countershock device 102 to operate for a single treatment scenario. The single treatment scenario is described in more detail below, but generally corresponds to countershock device delivering countershocks tor automated external defibrillation treatment during a single atrial fibrillation event. From a medical and practical standpoint, the power reserves needed may be only 10 minutes worth of power given that dire medical consequences result beyond 10 minutes in an atrial fibrillation event. In actuality, the single treatment battery may store power sufficient to provide countershocks for multiple atrial fibrillation events and/or for longer than 10 minutes, such as 20 to 60 minutes, or however much rime is deemed necessary from a safety factor standpoint.

In the present example, single treatment battery 104 is a lithium ion battery. However, the single treatment battery may be any currently known or later developed type of battery. The reader will appreciate that a variety of battery types exist and could be used in place of the single treatment battery shown in the figures, such as lithium ion batteries, nickel metal halide batteries, nickel cadmium batteries, and lead acid batteries. Additionally or alternatively to traditional batteries, the single treatment power storage component could be a fuel cell or capacitor. In addition to the types of batteries and power storage components existing currently, it is contemplated that the automated external defibrillator systems described herein could incorporate new types of batteries developed in the future.

The number of single treatment batteries in the automated external defibrillator system may be selected to meet the needs of a given application. The reader should understand dial the number of batteries may be different in other examples than is shown in the figures. For instance, some automated external defibrillator system examples include additional batteries than described in the present example.

The size and storage capacity of the single treatment battery may be varied as needed for a given application. In some examples, the single treatment battery is larger relative to the other components than depicted in the figures. In other examples, the single treatment battery is smaller relative to the other components than depicted in the figures. Further, the reader should understand that the single treatment battery and the other components may all be larger or smaller than described herein while maintaining their relative proportions.

In the present example, single treatment battery 104 is composed of lithium. However, the single treatment battery may be composed of any currently known or later developed material suitable for storing electrical energy.

Single Treatment Scenario

In the present example, the single treatment scenario corresponds to 10 minutes of automated external defibrillation treatment delivered by countershock device 102. However, the single treatment scenario also includes a predetermined safety margin of additional automated external defibrillation treatment beyond 10 minutes. In the example shown in FIGS. 1 and 2, the predetermined safety margin is up to 50 minutes of automated external defibrillation treatment delivered by countershock device 102 beyond the initial 10 minutes of automated external defibrillation treatment.

Charging Device

Charging device 107 serves to transfer power to single treatment battery 104 for single treatment battery 104 to store. The reader can see in FIGS. 1 and 2 that charging device 107 is configured to couple to single treatment battery 104. In particular, in the example shown in FIGS. 1 and 2 charging device 107 is configured to selectively couple to single treatment battery 104.

Figure 4:
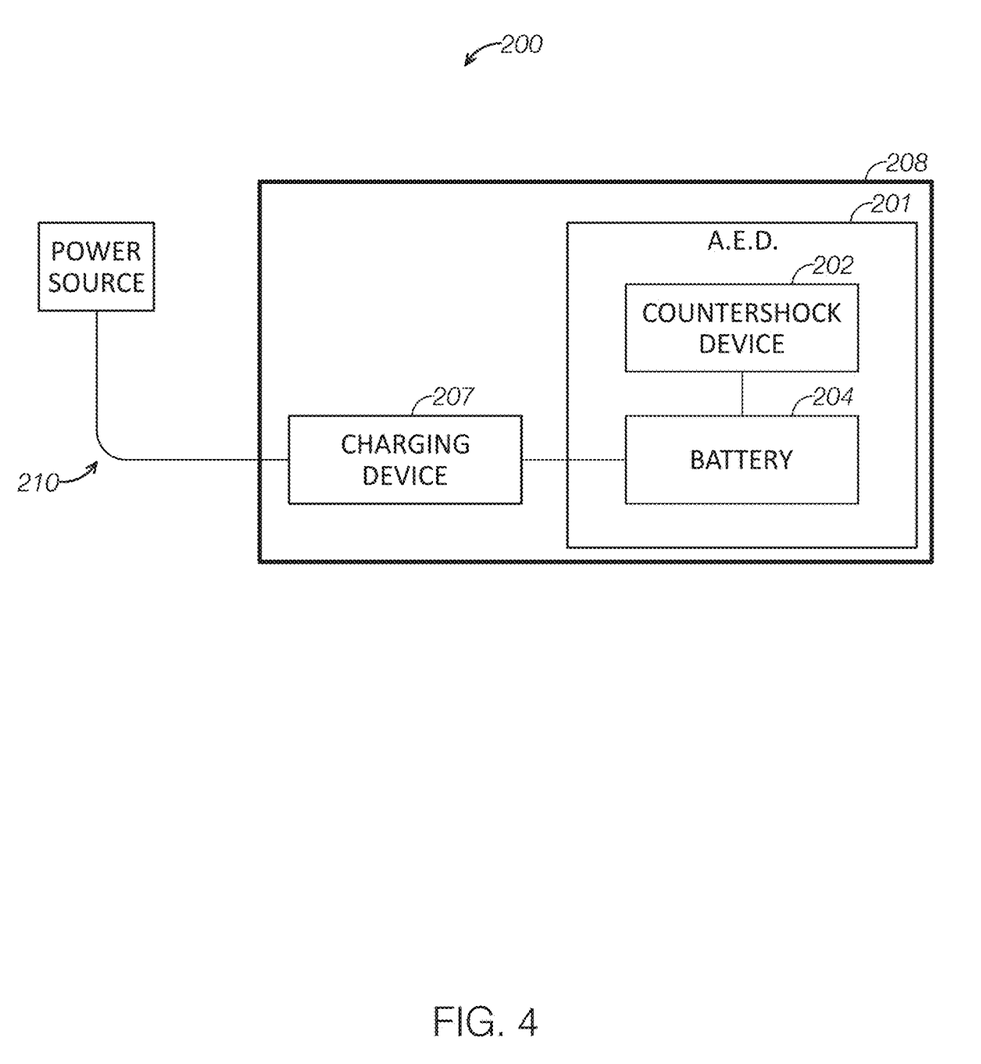
FIG. 4 is a schematic view of the AED system shown in FIG. 3 depicting a housing containing the AED device and the charging device, the AED device including a countershock device and a single Treatment battery fixedly coupled to the charging device, the charging device including a cable that extends outside the housing to couple to a power source.

As shown in FIGS. 1 and 2, charging device 107 is disposed outside housing 108 and is configured to be stored in vehicle 114 near automated external defibrillator 101. In other examples, such as shown in FIGS. 3-5, the charging device is disposed within a housing 208 containing an automated external defibrillator 201.

As depicted in FIGS. 1 and 2, charging device 107 includes a power connector 110 configured to electrically couple to external power source 111. In the example shown in FIG. 1, external power source 111 is a vehicle power source 118 in the form of a vehicle battery 113 electrically coupled to an auxiliary power socket 120. Accordingly, as shown in FIG. 1, charging device 107 is configured to operatively couple to vehicle power source 118 by power connector 110 being in the form of an auxiliary power outlet plug 113 complementarily configured with auxiliary power socket 120. Thus, charging device 107 is configured to operatively couple to vehicle battery 115.

The charging device and/or one or more other components of the automated external defibrillator system may derive from a modified form of a conventional device with an onboard charging component configured to draw power from a vehicle. For example, the charging device or other components could be a modified form of a device configured to jump-start a vehicle. Rather than use stored energy to jump-start a vehicle, the energy could be used by the automated external defibrillator to deliver countershock treatments to a person.

The number of charging devices in the automated external defibrillator system may be selected to meet the needs of a given application. The reader should understand that the number of charging devices may be different in other examples than is shown in the figures. For instance, some automated external defibrillator system examples include additional charging devices than described in the present example.

The size of the charging device may be varied as needed for a given application. In some examples, the charging device is larger relative to the other components than depicted in the figures. In other examples, the charging device is smaller relative to the other components than depicted in the figures. Further, the reader should understand that the charging device and the other components may all be larger or smaller than described herein while maintaining their relative proportions.

The shape of the charging device may be adapted to be different than the specific examples shown in the figures to suit a given application. For example, the charging device may include a face having the shape of a regular or irregular polygon, such as a circle, oval, triangle, square, rectangle pentagon, and the like. Additionally or alternatively, the charging device may include a face having an irregular shape. In three dimensions, the shape of the charging device may be a sphere, a pyramid, a cone, a cube, and variations thereof, such as a hemisphere or a frustoconical shape.

The charging device may be any currently known or later developed type of charging device. The reader will appreciate that a variety of charging device types exist and could be used in place of the charging device shown in the figures. In addition to the types of charging devices existing currently, it is contemplated that the automated external defibrillator systems described herein could incorporate new types of charging devices developed in the future.

Power Connector

Power connector 110 functions to electrically couple charging device 107 with external power source 111. As shown in FIG. 1, power connector 110 is in the form of vehicle auxiliary power outlet plug 113. In other examples, such as the example shown in FIGS. 3-5, the power connector is in the form of a universal serial bus connector.

The power connector may be any currently known or later developed type of power connector. The reader will appreciate that a variety of power connector types exist and could be used in place of the power connectors shown in the figures. Common power connection interfaces include universal serial bus (USB) connectors, micro-USB connectors, mini-USB connectors, and the like. In addition to the types of power connectors existing currently, it is contemplated that the automated external defibrillator systems described herein could incorporate new types of power connectors developed in the future.

Housing

As depicted in FIGS. 1 and 2, housing 108 contains automated external defibrillator 101. In the present example, housing 108 is composed of a polymer. However, the housing may be composed of any currently known or later developed material suitable for housing applications. Suitable materials include metals, polymers, ceramics, wood, and composite materials.

The size of the housing may be varied as needed for a given application. In some examples, the housing is larger relative to the other components than depicted in the figures. In other examples, the housing is smaller relative to the other components than depicted in the figures. Further, the reader should understand that the housing and the other components may all be larger or smaller than described herein while maintaining their relative proportions.

The shape of the housing may be adapted to be different than the specific examples shown in the figures to suit a given application. For example, the housing may include a face having the shape of a regular or irregular polygon, such as a circle, oval, triangle, square, rectangle pentagon, and the like. Additionally or alternatively, the housing may include a face having an irregular shape. In three dimensions, the shape of the housing may be a sphere, a pyramid, a cone, a cube, and variations thereof, such as a hemisphere or a frustoconical shape.

The number of housings in the automated external defibrillator system may be selected to meet the needs of a given application. The reader should understand that the number of housings may be different in other examples than is shown in the figures. For instance, some automated external defibrillator system examples include additional or fewer housings than described in the present example.

The housing may be any currently known or later developed type of housing. The reader will appreciate that a variety of housing types exist and could be used in place of the housing shown in the figures. In addition to the types of housings existing currently, it is contemplated that the automated external defibrillator systems described herein could incorporate new types of housings developed in the future.

Additional Embodiments

With reference to the figures not yet discussed in detail, the discussion will now focus on additional automated external defibrillator system embodiments. The additional embodiments include many similar or identical features to automated external defibrillator system 100. Thus, for the sake of brevity, each feature of the additional embodiments below will not be redundantly explained. Rather, key distinctions between the additional embodiments and automated external defibrillator system 100 will be described in detail and the reader should reference the discussion above for features substantially similar between the different system examples.

Second Embodiment

Turning attention to FIGS. 3-3, an automated external defibrillator system 200 will now be described as a second example of an automated external defibrillator system. As can be seen in FIGS. 3-5, automated external defibrillator system 200 includes an automated external defibrillator 201, a charging device 207, and a housing 208. Automated external defibrillator 201 includes a countershock device 202 and a single treatment battery 204.

With reference to FIGS. 3-5, a distinction between automated external defibrillator system 200 and automated external defibrillator system 100 is that charging device 207 is contained within housing 208 rather than outside the housing. The example shown in FIGS. 3-3 integrates automated external defibrillator 201 and charging device 207 into a single overall device contained within a common housing.

As shown in FIG. 4, charging device 207 is fixedly coupled to single treatment battery 204. Whereas charging device 107 was selectively coupled to single treatment battery 104, charging device 207 is more permanently coupled to single treatment battery 204.

The reader can see in FIG. 3 that power connector 210 includes a universal serial bus connector 212 rather than a vehicle auxiliary power outlet plug like in the FIG. 1 example. Universal serial bus connector 212 is configured to electrically couple and draw power from any device or power source with a universal serial bus port. In the example shown in FIG. 3, power connector 210 is electrically coupling charging device 207 to a computer 222. In particular, a by universal serial bus connector 212 of charging device 207 is selectively coupled to a universal serial bus port of computer 222.

The disclosure above encompasses multiple distinct inventions with independent utility. While each of these inventions has been disclosed in a particular form, the specific embodiments disclosed and illustrated above are nor to be considered in a limiting sense as numerous variations are possible. The subject matter of the inventions includes all novel and non-obvious combinations and subcombinations of the various elements, features, functions and/or properties disclosed above and inherent to those skilled in the art pertaining to such inventions. Where the disclosure or subsequently filed claims recite "a" element, "a first" element, or any such equivalent term, the disclosure or claims should be understood to incorporate one or more such elements, neither requiring nor excluding two or more such elements.

Applicant(s) reserves the right to submit claims directed to combinations and subcombinations of the disclosed inventions that are believed to be novel and non-obvious. Inventions embodied in other combinations and subcombinations of features, functions, elements and/or properties may be claimed through amendment of those claims or presentation of new claims in the present application or in a related application. Such amended or new claims, whether they are directed to the same invention or a different invention and whether they are different, broader, narrower or equal in scope to the original claims, are to be considered within the subject matter of the inventions described herein.

The invention claimed is:

1. An automated external defibrillator system, comprising:
   an automated external defibrillator not including a battery and including:
      a countershock device configured to deliver automated external defibrillation treatment to a person; and
      a single treatment capacitor electrically coupled to the countershock device, the single treatment capacitor having a power storage capacity selected to store power sufficient for the countershock device to operate for only a single treatment scenario, the single treatment capacitor configured to be rechargeable by an external power source; and
      a charging device configured to couple to the single treatment capacitor and to transfer power to the single treatment capacitor for the single treatment capacitor to store.

2. The automated external defibrillator system of claim 1, further comprising a housing containing the automated external defibrillator.

3. The automated external defibrillator system of claim 2, wherein the charging device is contained within the housing.

4. The automated external defibrillator system of claim 3, wherein the charging device is fixedly coupled to the single treatment capacitor.

5. The automated external defibrillator system of claim 2, wherein the charging device is disposed outside the housing.

6. The automated external defibrillator system of claim 5, wherein the charging device is selectively coupled to the single treatment capacitor.

7. The automated external defibrillator system of claim 5, wherein the charging device is a conventional device modified for use with the automated external defibrillator.

8. The automated external defibrillator system of claim 1, wherein the charging device includes a power connector configured to electrically couple to the external power source.

9. The automated external defibrillator system of claim 1, wherein the power connector includes a universal serial bus connector.

10. The automated external defibrillator system of claim 1, wherein the power connector includes a vehicle auxiliary power outlet plug.

11. The automated external defibrillator system of claim 1, wherein:
   the automated external defibrillator is configured to be stored in a vehicle; and
   the charging device is configured to be stored in the vehicle.

12. The automated external defibrillator system of claim 11, wherein:
   the vehicle includes a vehicle battery;
   the external power source is the vehicle battery; and
   the charging device is configured to operatively couple to the vehicle battery.

13. An automated external defibrillator system comprising:
   a housing;
   an automated external defibrillator contained within the housing, the automated external defibrillator not including a battery and including:
      a countershock device configured to deliver automated external defibrillation treatment to a person; and
      a single treatment capacitor electrically coupled to the countershock device, the single treatment capacitor having a power storage capacity selected to store power sufficient for the countershock device to operate for only a single treatment scenario, the single treatment capacitor configured to be rechargeable by an external power source;
   a charging device contained within the housing and electrically coupled to the single treatment capacitor, the charging device configured to transfer power to the single treatment capacitor for the single treatment capacitor to store.

14. The automated external defibrillator system of claim 13, wherein the external power source is a vehicle power source, and wherein the charging device is configured to operatively couple to the vehicle power source.

15. The automated external defibrillator system of claim 14, wherein the charging device includes a power connector configured to electrically couple to the vehicle power source.

16. An automated external defibrillator system comprising:
   a housing;
   an automated external defibrillator contained within the housing, the automated external defibrillator not including a battery and including:
      a countershock device configured to deliver automated external defibrillation treatment to a person; and
      a single treatment capacitor electrically coupled to the countershock, the single treatment capacitor having a power storage capacity selected to store power sufficient for the countershock device to operate for only a single treatment scenario, the single treatment capacitor configured to be rechargeable by an external power source; and
   a charging device disposed outside the housing and selectively electrically coupled to the single treatment capacitor, the charging device configured to transfer power to the single treatment capacitor for the single treatment capacitor to store.

17. The automated external defibrillator system of claim 16, wherein the charging device includes a power connector configured to electrically couple to a vehicle power source.

18. The automated external defibrillator system of claim 16, wherein the charging device is a conventional device modified for use with the automated external defibrillator.

19. The automated external defibrillator system of claim 18, wherein the conventional device is configured to jump-start a vehicle.

\* \* \* \* \*